US008859813B2

(12) United States Patent
Ignatyev et al.

(10) Patent No.: US 8,859,813 B2
(45) Date of Patent: Oct. 14, 2014

(54) IONIC LIQUIDS HAVING URONIUM CATIONS AND A PROCESS FOR MAKING SAME

(75) Inventors: Nikolai (Myloka) Ignatyev, Duisburg (DE); Urs Welz-Biermann, Heppenheim (DE); German Bissky, Wuppertal (DE); Helge Willner, Ruhr (DE); Andriy Kucheryna, Wuppertal (DE)

(73) Assignee: Merck Patent GmbH, Darmstadt (DE)

( * ) Notice: Subject to any disclaimer, the term of this patent is extended or adjusted under 35 U.S.C. 154(b) by 247 days.

(21) Appl. No.: 13/590,655

(22) Filed: Aug. 21, 2012

(65) Prior Publication Data
US 2012/0316058 A1 Dec. 13, 2012

Related U.S. Application Data

(62) Division of application No. 10/558,748, filed as application No. PCT/EP2004/005772 on May 28, 2004, now Pat. No. 8,269,041.

(30) Foreign Application Priority Data

Jun. 2, 2003 (DE) .................................. 103 24 891
Jun. 2, 2003 (DE) .................................. 103 25 050
Nov. 17, 2003 (DE) .................................. 102 53 758

(51) Int. Cl.
C07C 275/04 (2006.01)
C07F 9/28 (2006.01)
C07C 275/70 (2006.01)
C07F 9/30 (2006.01)
C07C 323/25 (2006.01)

(52) U.S. Cl.
CPC ............. C07C 323/25 (2013.01); C07F 9/28 (2013.01); C07C 275/70 (2013.01); C07F 9/301 (2013.01)
USPC .............. 564/63; 564/371; 564/372; 564/394

(58) Field of Classification Search
USPC .............................. 564/80, 394, 372, 63, 371
See application file for complete search history.

(56) References Cited

U.S. PATENT DOCUMENTS

| 3,721,581 | A | 3/1973 | Teramura et al. |
| 3,882,009 | A | 5/1975 | Wagener et al. |
| 4,214,096 | A | 7/1980 | Klingler et al. |
| 7,465,834 | B2 * | 12/2008 | Sueto et al. .................. 564/463 |

FOREIGN PATENT DOCUMENTS

| DE | 27 52 196 A1 | 6/1979 |
| DE | 196 48 125 | 5/1998 |

OTHER PUBLICATIONS

Database CA 'Online! Chemical Abstracts Service, Columbus, Ohio, US; Echner, Hartmut et al Echner, Hartmut et al: "Rapid thioester couplings mediated by new uronium salts Rapid thioester couplings mediated by new uranium salts" XP002302549 (1997).

Database CA "Online! Chemical Abstracts Service, Columbus, Ohio, US; Feith, Bernhard et al: Dication ethers. 11. Ambidoselective reactions of beta.-keto enolates with dication ethers" XP002302550 (1986).

Database CA 'Online! Chemical Abstracts Serivce, Columbus, Ohio, US; Feith Bernhard at al: "Ring-opening of N-(tetraalkylamidinio)pyridinium salts by anions of CH-acidic methylene compounds" XP002302551 (1986).

Kantiehner W et al: "Herstellung von 1,1,2,3,3-Pentasubsttluierten und 1,1,2,2,3,3-Hexasubstituierten Guanidiniumsalzen Sowie Von 1,1,2,3,3-Pentaalkylguanidinen preparation of 1,1,2,3,3-Penlasubstituted and 1,1,2,2,3,3-Hexasubstituted Guanidinium salts and 1,1,2,3,3-Pentaal" Liebigs Annalen Der Chemie, Verlag Chemie GMBH. Weinheim, DE, Bd. 108, 1984, Seiten 108-126, XP001194522.

Neibecker, D. et al Neibecker, D. et al: "Calionic .eta.3-allylic complexes, 4. Cationic.eta.3-ailylic complexes of nickel from S-allyl-1,1,3,3-tetramethylthiouronium salts Cationic. eta.3-allylic complexes. Cationic. eta.3-allylic complexes of nickel from S-allyl-1,1,3,3-tetramethylthiouronium salts" Inorganic Chemistry, 19(12), 3725-9 Coden: INOCAJ; ISSN: 0020-1669 Inorganic Chemistry, 19(12), 3725-9 Coden: INOCAJ; ISSN: 0020-1669, 1980, XP002302546.

Neibecker, D. et al: "Cationic.eta.3 allylic complexes. III. The reaction of S-allyl iso tetramethyl thiouronium salts with nickel tetracarbonyl" Tetrahedron Letters, (27), 2351-2-Coden: Teleay; ISSN: 0040-4039, 1977, XP002302547.

Database Beilstein Beilstein Institute for Organic Chemistry, Frankfurt-Main, DE; XP002302552 (1983).

Database Belstein Beilstein institute for Organic Chemistry, Frankfurt-Main, DE; XP002302553 (1995).

Database Beilstein Beilstein Institute for Organic Chemistry, Frankfurt-Main, DE; XP002302554 (1995).

Database Beilstein Beilstein Institute for Organic Chemistry, Frankfut-Main, DE; XP002302555 (1988).

Database CA 'Online! Chemical Abstracts Service, Columbus, Ohio, US; Habermann, Joerg et al Habermann, Joerg et al: Glycopeptide synthesis using 0-pentafluorophenyluronium salts as novel condensing reagents Glycopeptide synthesis using 0-pentafluorophenyluronium salts as novel condensing reagents; XP0023020556 (1998).

Scardovi, N. et al., Organic Letter, vol. 5, No. 10, 2003, pp. 1633-1635, XP002302548.

Mateus, Nuno M.M. et al., "Synthesis and properties of tetra-alkyl-dimethylguanidinium salts as a potential new generation of ionic liquids", Green Chemistry, 2003, 5, 347-352, pp. 347-352.

King, James Frederick et al., "Betylates. 4. The synthesis and preparative nucleophilic substitution reactions of alkyl S-[3]betylates[1]", 1983 National Research Council of Canada, pp. 235-243.

(Continued)

Primary Examiner — Fereydoun G Sajjadi
Assistant Examiner — Pancham Bakshi
(74) Attorney, Agent, or Firm — Millen, White, Zelano & Branigan, P.C.

(57) ABSTRACT

The present invention relates to salts having uronium cations and to a process for preparing same comprising alkylating urea $C(O)(NR_2)_2$ using an ester $AR°$.

12 Claims, No Drawings

(56) References Cited

OTHER PUBLICATIONS

Arbelot, M. et al., "Specific Molecular Orbital Contributions to Nucleophilicity. The Thiocarbonyl Group as Privileged Monitor to Pinpoint Active and Less Active Molecular Orbitals in Reactions with Methylating Agents", J. Org. Chem. 1995, 60, pp. 2330-2343.

Blanco, Jose M. et al., "Chiral Sulfinic Acids: Synthesis of Sodium (1S, 2S, 5R)-2-isopropyl-5-methylcyclohexanesulfinate by a Novel Route", Tetrahedron vol. 51, No. 3, pp. 935-940, 1995.

Mavrin, V. Yu. et al., "Reaction of Triheterosubstituted Carbonium Salts With Diethylphosphites", S.M. Kirov Kazan Chemical-Technology Institute. vol. 58, No. 9, pp. 2167-2168 (1987).

Habermann, Jörg at al., "Glycopeptide Synthesis Using O-Pentafluorophenyluronium Salts as Novel Condensing Reagents", J. prakt. Chem. 340 (1998) pp. 233-239.

Feith, Bernhard et al., "Ambidoselektive Reaktionen von β-Ketoenolaten mit Dikationethern", Liebigs Ann. Chem. 1986, pp. 2123-2141.

Feith, Bernhard et al., "Ringöffnung von N-(Tetraalkylamidinio)pyridinium-Salzen durch Anionen methylenaktiver Verbindungen", Chem. Ber. 119, pp. 3276-3296 (1986).

Kunz Horst Prof Dr, "New N,N,N',N'-tetra:substituted O-penta:fuirophonyl-uronium salts", espacenet, publication date: May 28, 1998; English Abstract of DE 19648125.

J. Japan Oil Chemists' Society, 1984, vol. 33, No. 11, 776-779—"Synthesis and Reactivity of Alkyloxy—and Alkyithiomethyteneiminium Salts" Kenji Nozaki at al.

English Abstract on p. 776 (first page)—J. Japan Oil Chemist's Society, 1984, vol. 33, No. 11, 776-779—"Synthesis and Reactivity of Alkyloxy—and Alkyithiomethyleneiminium Salts" Kenji Nozaki at al.

Llebigs Annalen der Chemie, 1980, No. 2, 246-252—"Investigation of the Effectiveness of Various 1-Dialkylemino-1-methoxycarbanium Methyl Sulfates in the Course of Acetalization" —Willi Kantiehner et al.

English Abstract on p. 246 (first page)—Liebigs Annalen der Chemie, 1980, No, 2, 246.252—"Investigation of the Effectiveness of Various 1-Dialkylamino-1-methoxycarbenium Methyl Sulfates in the Course of Acetalization"—Willi Kantlehner et al.

Organic Letters, 2001, vol. 3, No. 17, 2753-2756—"Stereoselective Synthesis of (Z)—Enethiols and Their Derivatives; Vinylic $S_N2$ Reaction of (E)—Alkenyl(pheny1)$\lambda^3$ iodanes with Thioamides" —Masahito Ochial et al.

J. Organometallic Chem., 1987, vol. 330, No. 1-2, 17-24 —"Unerwartetes Redoxverhalten Bei Cyclisierungsversuchen an o-Phenylendiphosphinderivaten"—K. Issleib et al.

Summary in English on p. 17 (first page)—J. Organometallic Chem., 1987, vol. 330, No, 1-2, 17-24 —"Unerwertetes Redoxverhalten Bei Cyclisierungsversuchen An o-Phenylendiphosphinderivalen" —,K. Issleib et al.

Tetrahedron, 1983, vol. 39, No. 3, 433-442—"O-Alkylation D'Amides A L'Aide De Sels D'Alkyidiptienylsulfonium"—M. Julia et al.

English Abstract on p. 433 (first page)—Tetrahedron, 1983, vol. 39, No. 3, 433-442—"O-Alkylation D'Amides A L'Aide De Sels D'Alkyldiphenylsulfonium"—M. Julia et al.

Zeitschrift für Naturforschung, B: Chemical Sciences, 1998, vol. 53, No. 8, 916-926—"[$R_2S$-$CH_2$OT$\eta$l+OTƒ as a Reagent with an Optionally Mono- or Bisetectrophilic $Csp^3$ Center"—Robert Weiss et al.

Zeitschrift für Naturforschung, B: Chemical Sciences, 1998, vol. 53, No. 5/6, 599-619—"Onia-Assisted $S_N2$—Reactions: General Access to Symmetrical and Unsymmetrical Geminally Bisonio Substituted Methane Derivatives"—Robert Weiss et al.

English Abstract on p. 599 (first page)—Zeitschrift für Naturforschung, B Chemical Sciences, 1998, vol. 53, No. 5/6, 599-619—"Onio-Assisted $S_N2$—Reactions: General Access to Symmetrical and Unsymmetrical Geminally Bisonio Substituted Methane Derivatives"—Robert Weiss et al.

* cited by examiner

IONIC LIQUIDS HAVING URONIUM CATIONS AND A PROCESS FOR MAKING SAME

This application is a divisional application of U.S. patent application Ser. No. 10/558,748, filed on Dec. 1, 2005.

The present invention relates to salts containing uronium or thiouronium cations and various anions, to processes for the preparation of these salts, and to the use thereof as ionic liquids.

Ionic liquids or liquid salts are ionic species which consist of an organic cation and a generally inorganic anion. They do not contain neutral molecules and generally have melting points below 373 K. A multiplicity of compounds which are used as ionic liquids are known in the prior art. Thus, solvent-free ionic liquids were disclosed for the first time by Hurley and Wier in a series of US patents (U.S. Pat. No. 2,446,331, U.S. Pat. No. 2,446,339 and U.S. Pat. No. 2,446,350). These "room temperature molten salts" were based on $AlCl_3$ and a multiplicity of n-alkylpyridinium halides.

In recent years, some review articles have been published on this topic (R. Sheldon "Catalytic reactions in ionic liquids", *Chem. Commun.*, 2001, 2399-2407; M. J. Earle, K. R. Seddon "Ionic liquids. Green solvent for the future", *Pure Appl. Chem.*, 72 (2000), 1391-1398; P. Wasserscheid, W. Keim "Ionische Flüssigkeiten—neue Lösungen für die Übergangsmetallkatalyse" [Ionic Liquids—Novel Solutions for Transition-Metal Catalysis], *Angew. Chem.*, 112 (2000), 3926-3945; T. Welton "Room temperature ionic liquids. Solvents for synthesis and catalysis", *Chem. Rev.*, 92 (1999), 2071-2083; R. Hagiwara, Ya. Ito. "Room temperature ionic liquids of alkylimidazolium cations and fluoroanions", *Journal of fluorine Chem.*, 105 (2000), 221-227).

The properties of ionic liquids, for example melting point, thermal and electrochemical stability, viscosity, are greatly influenced by the nature of the anion. By contrast, the polarity and hydrophilicity or lipophilicity can be varied through a suitable choice of the cation/anion pair. There is therefore a demand for novel ionic liquids having varied properties which facilitate additional possibilities with respect to their use.

The object of the present invention is to provide novel stable salt-like compounds having valuable properties which can be used as ionic liquids, and a process for the preparation thereof. In particular, the object of the present invention is to provide ionic compounds having very stable cations.

This object is achieved by the provision of salts having uronium or thiouronium cations in which the positive charge is delocalised over a plurality of hetero atoms according to the general formula (1)

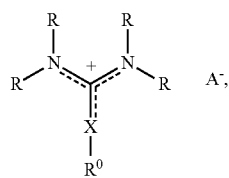

in which
X denotes O or S,
in which the substituents R and $R^0$ each, independently of one another, have the meaning of
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds
saturated, partially or fully unsaturated cycloalkyl having 3-7 C atoms,
which may be substituted by alkyl groups having 1-6 C atoms,
and R may also denote hydrogen,
where one or more substituents R or $R^0$ may be partially or fully substituted by halogen or partially by CN or $NO_2$, but where halogenation in the α-position in $R^0$ is excluded, and
halogen denotes F, Cl, Br or I,
where the substituents R and $R^0$ may be connected to one another in pairs by a single or double bond
and where one carbon atom or two non-adjacent carbon atoms of one or more substituents R or $R^0$ which are not directly adjacent to the hetero atom may be replaced by atoms and/or atom groups selected from the group —O—, —C(O)—, —C(O)O—, —S—, —S(O)—, —$SO_2$—, —$SO_3$—, —N=, —N=N—, —NH—, —NR'—, —PR'—, —P(O)R'—, —P(O)R'—O—, —O—P(O)R'—O—, and —P(R')$_2$=N—, where R' is unfluorinated, partially or perfluorinated alkyl having 1-6 C atoms, saturated or partially unsaturated cycloalkyl having 3-7 C atoms, unsubstituted or substituted phenyl or an unsubstituted or substituted heterocycle,
and
A- is selected from the group consisting of:
$[R^1SO_3]^-$, $[R^{F'}SO_3]^-$, $[(R^FSO_2)_2N]^-$, $[(R^FSO_2)_3C]^-$, $[(FSO_2)_3C]^-$, $[R^1CH_2OSO_3]^-$, $[R^1C(O)O]^-$, $[R^{F'}C(O)O]^-$, $[CCl_3C(O)O]^-$, $[(CN)_3C]^-$, $[(CN)_2CR^1]^-$, $[(R^1O(O)C)_2CR^1]^-$, $[P(C_nF_{2n+1-m}H_m)_yF_{6-y}]^-$, $[P(C_6F_5)_yF_{6-y}]^-$, $[R^1{}_2P(O)O]^-$, $[R^1P(O)O_2]^{2-}$, $[(R^1O)_2P(O)O]^-$, $[(R^1O)P(O)O_2]^{2-}$, $[(R^1O)(R^1)P(O)O]^-$, $[R^F{}_2P(O)O]^-$, $[R^FP(O)O_2]^{2-}$, $[BF_xR^F{}_{4-z}]^-$, $[BF_z(CN)_{4-z}]^-$, $[B(CN)_4]^-$, $[B(C_6F_5)_4]^-$, $[B(OR^1)_4]^-$, $[N(CF_3)_2]^-$, $[N(CN)_2]^-$, $[AlCl_4]^-$ or $[SiF_6]^{2-}$,
where the substituents $R^F$ and $R^{F'}$ each, independently of one another, the meaning of
perfluorinated and straight-chain or branched alkyl having 1-20 C atoms, where the trifluoromethyl group is excluded for $R^{F'}$,
perfluorinated and straight-chain or branched alkenyl having 2-20 C atoms and one or more double bonds,
perfluorinated phenyl and saturated, partially or fully unsaturated cycloalkyl having 3-7 C atoms, which may be substituted by perfluoroalkyl groups,
where the substituents $R^F$ or $R^{F'}$ may be connected to one another in pairs by a single or double bond and
where one carbon atom or two non-adjacent carbon atoms of the substituent $R^F$ or $R^{F'}$ which are not in the α-position to the hetero atom may be replaced by atoms and/or atom groups selected from the group —O—, —C(O)—, —S—, —S(O)—, —$SO_2$—, —N=, —N=N—, —NR'—, —PR'— and —P(O)R'— or may have an end group R'—O—$SO_2$— or R'—O—C(O)—, where R' denotes unfluorinated, partially or perfluorinated alkyl having 1-6 C atoms, saturated or partially unsaturated cycloalkyl having 3-7 C atoms, unsubstituted or substituted phenyl or an unsubstituted or substituted heterocycle
and
where the substituents $R^1$ each, independently of one another, the meaning of
hydrogen in the case where $A^-=[(CN)_2CR^1]^-$ or $[(R^1O(O)C)_2CR^1]^-$ and X=O or S, or
hydrogen in the case where $A^-=[R^1CH_2OSO_3]^-$, X=S or O and the substituents R and $R^0$=alkyl groups having 1 to 20 C atoms, straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms,
which may be substituted by alkyl groups having 1-6 C atoms,
where the substituents $R^1$ may be partially substituted by CN, $NO_2$ or halogen and
halogen denotes F, Cl, Br or I,
where the substituents $R^1$ may be connected to one another in pairs by a single or double bond and
where one carbon atom or two non-adjacent carbon atoms of the substituent $R^1$ which are not in the α-position to the hetero atom may be replaced by atoms and/or atom groups selected from the group —O—, —C(O)—, —C(O)O—, —S—, —S(O)—, —$SO_2$—, —$SO_3$—, —N=, —N=N—, —NH—, —NR'—, —PR'— and —P(O)R'—(O)R'—, (P(O)R'O—, OP(O)R'O—, —PR'$_2$=N—, —C(O)NH—, —C(O)NR'—, —$SO_2$NH— or —$SO_2$NR'—, where R' denotes unfluorinated, partially or perfluorinated alkyl having 1-6 C atoms, saturated or partially unsaturated cycloalkyl having 3-7 C atoms, unsubstituted or substituted phenyl or an unsubstituted or substituted heterocycle
and the variables
n denotes 1 to 20,
m denotes 0, 1, 2 or 3,
y denotes 0, 1, 2, 3, or 4,
z denotes 0, 1, 2 or 3,
with the proviso that
for X=S and R and $R^0$=alkyl groups having 1 to 20 C atoms, the anions
$A^-$=$[BF_4]^-$, $CF_3COO^-$, $[B(C_6H_5)_4]^-$ or $[CH_3C_6H_4SO_3]^-$ are to be allowed
and
for X=O, the anions $A^-$=$CF_3COO^-$ and $[B(C_6H_5)_4]^-$ are to be allowed and
for X=O and $R^0$=ethyl, the anion $A^-$=$CH_3CH_2OSO_3^-$ is to be excluded.

For the purposes of the present invention, fully unsaturated substituents are also taken to mean aromatic substituents.

The compounds according to the invention are distinguished, in particular, by very stable cations.

The compounds according to the invention are accordingly salts which have optionally substituted thiouronium or uronium cations.

Besides hydrogen, suitable substituents R are, in accordance with the invention: $C_1$- to $C_{20}$-, in particular $C_1$- to $C_{12}$-alkyl groups, $C_2$- to $C_{20}$-, in particular $C_2$- to $C_{12}$-, alkenyl or alkynyl groups and saturated or unsaturated, i.e. also aromatic, $C_3$- to $C_7$-cycloalkyl groups, which may be substituted by $C_1$- to $C_6$-alkyl groups, in particular phenyl.

The four substituents R of the salts according to the invention may be identical or different.

Suitable in accordance with the invention as substituent $R^0$ are: $C_1$- to $C_{20}$-, in particular $C_1$- to $C_{12}$-alkyl groups, $C_2$- to $C_{20}$-, in particular $C_2$- to $C_{12}$-, alkenyl or alkynyl groups and saturated or unsaturated, i.e. also aromatic, $C_3$- to $C_7$-cycloalkyl groups, which may be substituted by $C_1$- to $C_6$-alkyl groups, in particular phenyl.

The $C_1$-$C_{12}$-alkyl group is, for example, methyl, ethyl, isopropyl, propyl, butyl, sec-butyl or tert-butyl, furthermore also pentyl, 1-, 2- or 3-methylbutyl, 1,1-, 1,2- or 2,2-dimethylpropyl, 1-ethylpropyl, hexyl, heptyl, octyl, nonyl, decyl, undecyl or dodecyl. Optionally also partially or fully substituted by F, for example difluoromethyl, trifluoromethyl, trifluoroethyl, pentafluoroethyl, pentafluoropropyl, heptafluoropropyl, heptafluorobutyl, nonafluorobutyl or nonafluorohexyl.

Preferred alkyl groups as described above have 1 to 6 C atoms.

Unsubstituted saturated or partially or fully unsaturated cycloalkyl groups having 3-7 C atoms are therefore cyclopropyl, cyclobutyl, cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, which may be substituted by $C_1$- to $C_6$-alkyl groups, where the cycloalkyl group or the cycloalkyl group substituted by $C_1$- to $C_6$-alkyl groups may in turn also be substituted by halogen atoms, such as F, Cl, Br or I, in particular F or Cl, CN or $NO_2$.

The substituents R and $R^0$ may be partially or fully substituted by halogen atoms, in particular by F and/or Cl, or partially by CN or $NO_2$, where halogenation of the α-$CH_2$ group of $R^2$ is excluded. Furthermore, the substituents R or $R^0$ may contain one or two mutually non-adjacent hetero atoms or atom groups selected from the group —O—, —C(O)—, —C(O)O—, —S—, —S(O)—, —$SO_2$—, —$SO_2$O—, —N=, —N=N—, —NH—, —NR'—, —PR'—, —P(O)R'—, —P(O)R'—O—, —O—P(O)R'—O—, —P(O)(NR'$_2$)—NR'— and —PR'$_2$=N—, where R' can be an unfluorinated, partially or perfluorinated $C_1$- to $C_6$-alkyl, $C_3$- to $C_7$-cycloalkyl, unsubstituted or substituted phenyl or an unsubstituted or substituted heterocycle.

In R', $C_3$- to $C_7$-cycloalkyl is, for example, cyclopropyl, cyclobutyl, cyclopentyl, cyclohexyl or cycloheptyl.

In R', substituted phenyl denotes phenyl which is substituted by $C_1$- to $C_6$-alkyl, $C_1$- to $C_6$-alkenyl, $NO_2$, F, Cl, Br, I, OH, $C_1$-$C_6$-alkoxy, CN, SCN, $SCF_3$, $SO_2CF_3$, C(O)O—$C_1$-$C_6$-alkyl, $NH_2$, $C_1$-$C_6$-alkylamino or $C_1$-$C_6$-dialkylamino, COOH, C(O)NR"$_2$, $SO_2$OR", $SO_2$X', $SO_2$NR"$_2$, $SO_3$H or NHC(O)R", where X' denotes F, Cl or Br and R" denotes an unfluorinated, partially or perfluorinated $C_1$- to $C_6$-alkyl or $C_3$- to $C_7$-cycloalkyl as defined for R', for example, o-, m- or p-methylphenyl, o-, m- or p-ethylphenyl, o-, m- or p-propylphenyl, o-, m- or p-isopropylphenyl, o-, m- or p-tert-butylphenyl, o-, m- or p-aminophenyl, o-, m- or p-(N,N-dimethylamino)phenyl, o-, m- or p-nitrophenyl, o-, m- or p-hydroxyphenyl, o-, m- or p-methoxyphenyl, o-, m- or p-ethoxyphenyl, o-, m-, p-(trifluoromethyl)phenyl, o-, m-, p-(trifluoromethoxy)phenyl, o-, m-, p-(trifluoromethylsulfonyl)phenyl, o-, m- or p-fluorophenyl, o-, m- or p-chlorophenyl, o-, m- or p-bromophenyl, o-, m- or p-iodophenyl, furthermore preferably 2,3-, 2,4-, 2,5-, 2,6-, 3,4- or 3,5-dimethylphenyl, 2,3-, 2,4-, 2,5-, 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethylphenyl.

In R' heterocycle is taken to mean a saturated or unsaturated mono- or bicyclic heterocyclic radical having 5 to 13 ring members, where 1, 2 or 3 N and/or 1 or 2 S or O atoms may be present and the heterocyclic radical may be mono- or polysubstituted by $C_1$- to $C_6$-alkyl, $C_1$- to $C_6$-alkenyl, $NO_2$, F, Cl, Br, I, OH, $C_1$-$C_6$-alkoxy, CN, SCN, $SCF_3$, $SO_2CF_3$, C(O)O—$C_1$-$C_6$-alkyl, $NH_2$, $C_1$-$C_6$-alkylamino or $C_1$-$C_6$-dialkylamino, COOH, C(O)NR"$_2$, SO$_2$OR", SO$_2$X', SO$_2$NR"$_2$, SO$_3$H or NHC(O)R", where X' and R" have a meaning indicated above.

The heterocyclic radical is preferably substituted or unsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1H-indolyl, 1-, 2-, 4- or 5-benzimidazolyl, 1-, 3-, 4-, 5-, 6-, or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl or 1-, 2- or 3-pyrrolidinyl.

Without restricting generality, examples of substituents R and R$^0$ of the thiouronium or uronium cation are:

—CH$_3$, —C$_2$H$_5$, —C$_3$H$_7$, —CH(CH$_3$)$_2$, —C$_4$H$_9$, —C(CH$_3$)$_3$, —C$_5$H$_{11}$, —C$_6$H$_{13}$, —C$_7$H$_{15}$, —C$_8$H$_{17}$, —C$_9$H$_{19}$, —C$_{10}$H$_{21}$, —C$_{12}$H$_{25}$, —C$_{20}$H$_{41}$, —OCH$_3$, —OCH(CH$_3$)$_2$, —CH$_2$OCH$_3$, —CH$_2$OCH(CH$_3$)$_2$, —C$_2$H$_4$SC$_2$H$_5$, —C$_2$H$_4$SCH(CH$_3$)$_2$, —S(O)CH$_3$, —SO$_2$CH$_3$, —SO$_2$CH$_3$, —SO$_2$C$_6$H$_5$, —SO$_2$C$_3$H$_7$, —SO$_2$CH(CH$_3$)$_2$, —SO$_2$CH$_2$CF$_3$, —CH$_2$SO$_2$CH$_3$, —CH$_2$N(H)C$_2$H$_5$, —C$_2$H$_4$N(H)C$_2$H$_5$, —CH$_2$N(CH$_3$)CH$_3$, —CN, —C$_2$H$_4$N(CH$_3$)CH$_3$, —CF$_3$, —C$_2$F$_5$, —C$_3$F$_7$, —C$_4$F$_9$, —C(CF$_3$)$_3$, —CF$_2$SO$_2$CF$_3$, —C$_2$F$_4$N(C$_2$F$_5$)C$_2$F$_5$, —CHF$_2$, —CH$_2$CF$_3$, —C$_2$F$_2$H$_3$, —C$_3$FH$_6$, —CH$_2$C$_3$F$_7$, —C(CFH$_2$)$_3$, —CH$_2$C(O)OH, —CH$_2$C$_6$H$_5$, —CH$_2$C(O)CH$_3$, —CH$_2$C(O)C$_2$H$_5$, —CH$_2$C(O)OCH$_3$, —CH$_2$C(O)OC$_2$H$_5$, —C(O)CH$_3$, —C(O)C$_6$H$_5$, —C(O)OCH$_3$, —C(O)OC$_2$H$_5$, P(O)(C$_2$H$_5$)$_2$, P(O)[N(C$_2$H$_5$)$_2$]$_2$,

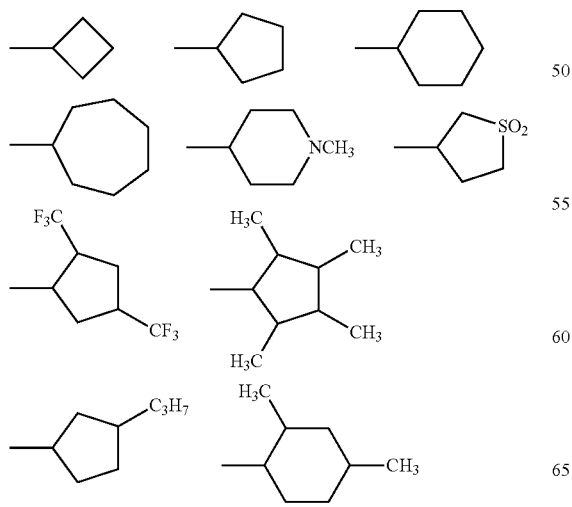

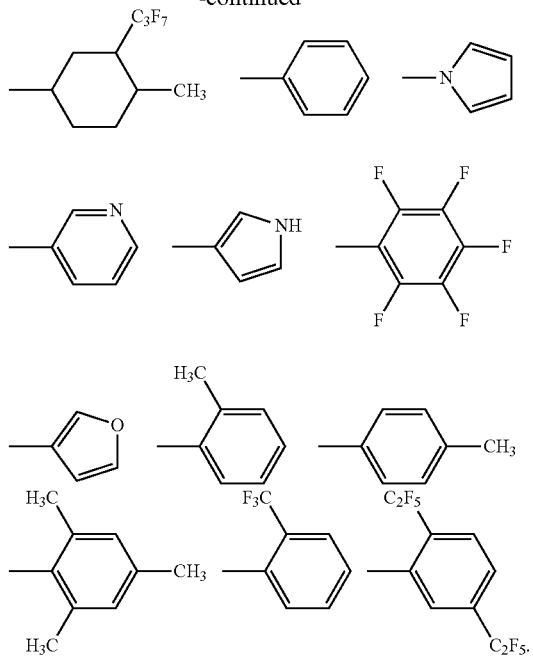

Up to four substituents R may also be connected in pairs in such a way that mono-, bi- or polycyclic cations are formed.

Without restricting generality, examples of such cations are:

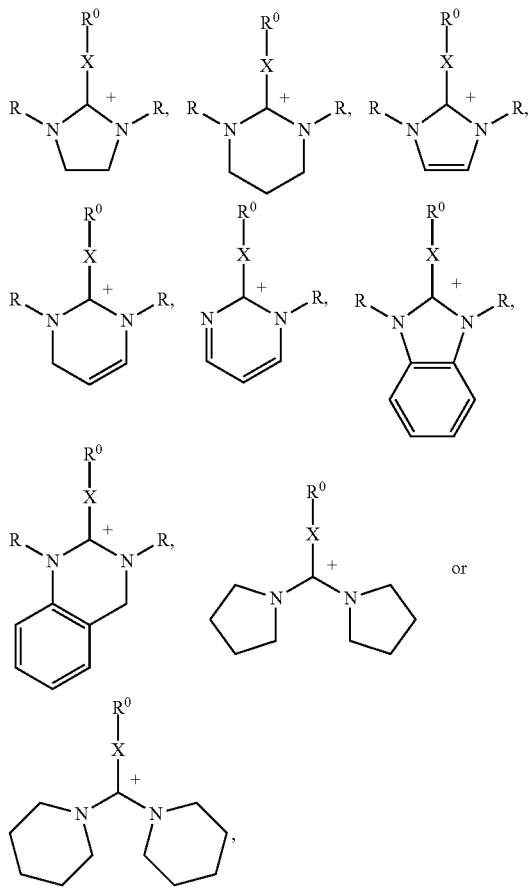

where the substituents R and $R^0$ can have a meaning indicated above or a particularly preferred meaning. The carbocycles or heterocycles of the cations indicated above may optionally also be substituted by $C_1$- to $C_6$-alkyl $C_1$- to $C_6$-alkenyl, $NO_2$, F, Cl, Br, I, OH, $C_1$-$C_6$-alkoxy, CN, SCN, $SCF_3$, $SO_2CF_3$, $C(O)O$—$C_1$-$C_6$-alkyl, $NH_2$, $C_1$-$C_6$-akylamino or $C_1$-$C_6$-dialkylamino, COOH, $C(O)NR''_2$, $SO_2OR''$, $SO_2NR''_2$, $SO_2X'$, $SO_3H$ or $NHC(O)R''$ or substituted or unsubstituted phenyl or an unsubstituted or substituted heterocycle, where X' and R'' have a meaning indicated above.

The anion $A^-$ of the salts according to the invention is selected from $[R^1SO_3]^-$, $[R^{F'}SO_3]^-$, $[(R^FSO_2)_2N]^-$, $[(R^FSO_2)_3C]^-$, $[(FSO_2)_3C]^-$, $[R^1CH_2OSO_3]^-$, $[R^1C(O)O]^-$, $[R^{F'}C(O)O]^-$, $[CCl_3C(O)O]^-$, $[(CN)_3C]^-$, $[(CN)_2CR^1]^-$, $[(R^1O(O)C)_2CR^1]^-$, $[P(C_nF_{2n+1-m}H_m)_yF_{6-y}]^-$, $[P(C_6F_5)_yF_{6-y}]^-$, $[R^1_2P(O)O]^-$, $[R^1P(O)O_2]^{2-}$, $[(R^1O)_2P(O)O]^-$, $[(R^1O)P(O)O_2]^{2-}$, $[(R^1O)(R^1)P(O)O]^-$, $[R^F_2P(O)O]^-$, $[R^FP(O)O_2]^{2-}$, $[BF_zR^F_{4-z}]^-$, $[BF_z(CN)_{4-z}]^-$, $[B(CN)_4]^-$, $[B(C_6F_5)_4]^-$, $[B(OR^1)_4]^-$, $[N(CF_3)_2]^-$, $[N(CN)_2]^-$, $[AlCl_4]^-$ or $[SiF_6]^{2-}$, where the substituents $R^F$ and $R^{F'}$ each, independently of one another, the meaning of perfluorinated and straight-chain or branched alkyl having 1-20 C atoms, where the trifluoromethyl group is excluded for $R^{F'}$, perfluorinated and straight-chain or branched alkenyl having 2-20 C atoms and one or more double bonds, perfluorinated phenyl and saturated, partially or fully unsaturated cycloalkyl having 3-7 C atoms, which may be substituted by perfluoroalkyl groups, where the substituents $R^F$ or $R^{F'}$ may be connected to one another in pairs by a single or double bond and where one carbon atom or two non-adjacent carbon atoms of the substituent $R^F$ or $R^{F'}$ which are not in the α-position to the hetero atom may be replaced by atoms and/or atom groups selected from the group —O—, —C(O)—, —S—, —S(O)—, —SO_2—, —N=, —N=N—, —NR'—, —PR'— and —P(O)R'— or may have an end group R'—O—SO_2— or R'—O—C(O)—, where R' denotes unfluorinated, partially or perfluorinated alkyl having 1-6 C atoms, saturated or partially unsaturated cycloalkyl having 3-7 C atoms, unsubstituted or substituted phenyl or an unsubstituted or substituted heterocycle and where the substituents $R^1$ each, independently of one another, the meaning of hydrogen in the case where $A^-=[(CN)_2CR^1]^-$ or $[(R^1O(O)C)_2CR^1]^-$ and X=O or S, or hydrogen in the case where $A^-=[R^1CH_2OSO_3]^-$, X=S or O and the substituents R and $R^0$=alkyl groups having 1 to 20 C atoms, straight-chain or branched alkyl having 1-20 C atoms, straight-chain or branched alkenyl having 2-20 C atoms and one or more double bonds, straight-chain or branched alkynyl having 2-20 C atoms and one or more triple bonds saturated, partially or fully unsaturated cycloalkyl having 3-7 C atoms, which may be substituted by alkyl groups having 1-6 C atoms, where the substituents $R^1$ may be partially substituted by CN, $NO_2$ or halogen and halogen denotes F, Cl, Br or I, where the substituents $R^1$ may be connected to one another in pairs by a single or double bond and where one carbon atom or two non-adjacent carbon atoms of the substituent $R^1$ which are not in the α-position to the hetero atom may be replaced by atoms and/or atom groups selected from the group —O—, —C(O)—, —C(O)O—, —S—, —S(O)—, —SO_2—, —SO_3—, —N=, —N=N—, —NH—, —NR'—, —PR'— and —P(O)R'—, (P(O)R'O—, OP(O)R'O—, —PR'_2=N—, —C(O)NH—, —C(O)NR'—, —SO_2NH— or —SO_2NR'—, where R' denotes unfluorinated, partially or perfluorinated alkyl having 1-6 C atoms, saturated or partially unsaturated cycloalkyl having 3-7 C atoms, unsubstituted or substituted phenyl or an unsubstituted or substituted heterocycle and the variables n denotes 1 to 20, m denotes 0, 1, 2 or 3, y denotes 0, 1, 2, 3, or 4, z denotes 0, 1, 2 or 3, with the proviso that for X=S and R and $R^0$=alkyl groups having 1 to 20 C atoms, the anions $A^-=[BF_4]^-$, $CF_3COO^-$, $[B(C_6H_5)_4]^-$ or $[CH_3C_6H_4SO_3]^-$ are to be allowed and for X=O, the anions $A^-CF_3COO^-$ and $[B(C_6H_5)_4]^-$ are to be allowed and for X=O and $R^0$=ethyl, the anion $A^-=CH_3CH_2OSO_3^-$ is to be excluded.

A straight-chain or branched alkenyl having 2 to 20 C atoms, where a plurality of double bonds may also be present, is, for example, allyl, 2- or 3-butenyl, isobutenyl, sec-butenyl, furthermore 4-pentenyl, isopentenyl, hexenyl, heptenyl, octenyl, —$C_9H_{17}$, —$C_{10}H_{19}$ to —$C_{20}H_{39}$; preferably allyl, 2- or 3-butenyl, isobutenyl, sec-butenyl, preference is furthermore given to 4-pentenyl, isopentenyl or hexenyl.

A straight-chain or branched alkynyl having 2 to 20 C atoms, where a plurality of triple bonds may also be present, is, for example, ethynyl, 1- or 2-propynyl, 2- or 3-butynyl, furthermore 4-pentynyl, 3-pentynyl, hexynyl, heptynyl, octynyl, —$C_9H_{15}$, —$C_{10}H_{17}$ to —$C_{20}H_{37}$, preferably ethynyl, 1- or 2-propynyl, 2- or 3-butynyl, 4-pentynyl, 3-pentynyl or hexynyl.

In the case where a plurality of $R^F$ or $R^{F'}$ are present in an anion, these may also be connected in pairs by single or double bonds in such a way that bi- or polycyclic anions are formed.

Furthermore, the substituents $R^F$ or $R^{F'}$ may contain one or two mutually non-adjacent atoms or atom groups which are not in the α-position to the hetero atom selected from the group —O—, —SO_2— and —NR'— or the end group —$SO_2X'$, where R' can be=unfluorinated, partially or perfluorinated $C_1$- to $C_6$-alkyl, $C_3$- to $C_7$-cycloalkyl, unsubstituted or substituted phenyl, including —$C_6F_5$, or an unsubstituted or substituted heterocycle and X'=F, Cl or Br.

Without restricting generality, examples of substituents $R^F$ and $R^{F'}$ of the anion are:

—$CF_3$, —$C_2F_5$, —$C_3F_7$, —$C_4F_9$, —$C(CF_3)_3$, —$CF_2N(CF_3)CF_3$, —$CF_2OCF_3$, —$CF_2S(O)CF_3$, —$CF_2SO_2CF_3$, —$C_2F_4N(C_2F_5)C_2F_5$, $CF=CF_2$, —$C(CF_3)=CFCF_3$, —$CF_2CF=CFCF_3$, —$CF=CFN(CF_3)CF_3$ or —$CF_2SO_2F$, —$C(CF_3)=CFCF_3$, —$CF_2CF=CFCF_3$ or —$CF=CFN(CF_3)CF_3$.

$R^{F'}$ is preferably pentafluoroethyl, heptafluoropropyl or nonafluorobutyl. $R^F$ is preferably trifluoromethyl, pentafluoroethyl, heptafluoropropyl or nonafluorobutyl.

With the restriction of the disclaimer in Claim 1, some examples of anions according to the invention are indicated below:

—[CF$_3$SO$_3$]$^-$, [CF$_3$CF$_2$SO$_3$]$^-$, [CH$_3$CH$_2$SO$_3$]$^-$, [CF$_3$SO$_2$)$_2$N]$^-$, [(C$_2$F$_5$SO$_2$)$_2$N]$^-$, [(CF$_3$SO$_2$)$_3$C]$^-$, [(C$_2$F$_5$SO$_2$)$_3$C]$^-$, [CH$_3$CH$_2$OSO$_3$]$^-$, [(FSO$_2$)$_3$C]$^-$, [CF$_3$C(O)O]$^-$, [CF$_3$CF$_2$C(O)O]$^-$, [CH$_3$CH$_2$C(O)O]$^-$, [CH$_3$C(O)O]$^-$, [P(C$_2$F$_5$)$_3$F$_3$]$^-$, [P(CF$_3$)$_3$F$_3$]$^-$, [P(C$_2$F$_4$H)(CF$_3$)$_2$F$_3$]$^-$, [P(C$_2$F$_3$H$_2$)$_3$F$_3$]$^-$, [P(C$_2$F$_5$)(CF$_3$)$_2$F$_3$]$^-$, [P(C$_6$F$_5$)$_3$F$_3$]$^-$, [P(C$_3$F$_7$)$_3$F$_3$]$^-$, [P(C$_4$F$_9$)$_3$F$_3$]$^-$, [P(C$_2$F$_5$)$_2$F$_4$]$^-$, [(C$_2$F$_5$)$_2$P(O)O]$^-$, [(C$_2$F$_5$)P(O)O$_2$]$^{2-}$, [P(C$_6$F$_5$)$_2$F$_4$]$^-$, [(CF$_3$)$_2$P(O)O]$^-$, [(CH$_3$)$_2$P(O)O]$^-$, [(C$_4$F$_9$)$_2$P(O)O]$^-$, [CF$_3$P(O)O$_2$]$^{2-}$, [CH$_3$P(O)O$_2$]$^{2-}$, [(CH$_3$O)$_2$P(O)O]$^-$, [BF$_3$(CF$_3$)]$^-$, [BF$_2$(C$_2$F$_5$)$_2$]$^-$, [BF$_3$(C$_2$F$_5$)]$^-$, [BF$_2$(CF$_3$)$_2$]$^-$, [B(C$_2$F$_5$)$_4$]$^-$, [BF$_3$(CN)]$^-$, [BF$_2$(CN)$_2$]$^-$, [B(CN)$_4$]$^-$, [B(CF$_3$)$_4$]$^-$, [BF$_4$]$^-$, [B(OCH$_3$)$_4$]$^-$, [B(OCH$_3$)$_2$(OC$_2$H$_5$)]$^-$, [B(O$_2$C$_2$H$_4$)$_2$]$^-$, [B(O$_2$C$_2$H$_2$)$_2$]$^-$, [B(O$_2$CH$_4$)$_2$]$^-$, [N(CF$_3$)$_2$]$^-$, [N(CN)$_2$]$^-$, [C(CN)$_3$]$^-$, [AlCl$_4$]$^-$ or [SiF$_6$]$^{2-}$.

Particularly preferred anions from this group taking into account the disclaimers are [R$^F$SO$_3$]$^-$, [P(C$_n$F$_{2n+1-m}$H$_m$)$_y$F$_{6-y}$]$^-$, [R$^F$$_2$P(O)O]$^-$, [BF$_z$R$^F$$_{4-z}$]$^-$ or [BF$_z$(CN)$_{4-n}$]$^-$, where n, m, y and z have one of the above-mentioned meanings, for example [B(CN)$_4$]$^-$, [(C$_2$F$_5$)$_3$PF$_3$]$^-$, [(C$_2$F$_5$)$_2$PF$_4$]$^-$, [C$_4$F$_9$)$_3$PF$_3$]$^-$, [(C$_3$F$_7$)$_3$PF$_3$]$^-$, [B(C$_2$F$_5$)F$_3$]$^-$, [(CF$_3$)$_2$P(O)O]$^-$, [(C$_2$F$_5$)$_2$P(O)O]$^-$ or [B(CF$_3$)$_4$]$^-$. Very particularly preferred anions from this group taking into account the disclaimers are [BF$_4$]$^-$, [(C$_2$F$_5$)$_3$PF$_3$]$^-$, [(C$_2$F$_5$)$_2$P(O)O]$^-$ or [CF$_3$SO$_3$]$^-$.

Of the particularly preferred anions, the phosphates of the formula [P(C$_n$F$_{2n+1-m}$H$_m$)$_y$F$_{6-y}$]$^-$ have a particular meaning since the choice of this anion results in salts of the formula (1) of particularly low viscosity.

Preference is given in accordance with the invention to a group of salts of the formula (1) in which the substituents R of the cation denote hydrogen or a straight-chain or branched alkyl group having 1-12 C atoms, in particular having 1-6 C atoms, and A$^-$ has a meaning indicated for the formula (1) or a meaning indicated as preferred or particularly preferred.

Preference is given in accordance with the invention to a group of salts of the formula (1) in which the substituents R of the cation are selected from the group methyl, ethyl, n-propyl, isopropyl, n-butyl, tert-butyl, sec-butyl, phenyl and cyclohexyl, and A$^-$ has a meaning indicated for the formula (1) or a meaning indicated as preferred or particularly preferred.

Preference is given in accordance with the invention to a group of salts of the formula (1) in which X denotes sulfur and A$^-$ has a meaning indicated for the formula (1) or a meaning indicated as preferred or particularly preferred.

Preference is given in accordance with the invention to a group of salts of the formula (1) in which X denotes oxygen and A$^-$ has a meaning indicated for the formula (1) or a meaning indicated as preferred or particularly preferred.

Preference is given in accordance with the invention to a group of salts of the formula (1) in which R$^0$ denotes a straight-chain or branched alkyl group having 1-20 C atoms, which may be partially or fully fluorinated, but where fluorination of the α-CH$_2$ group of R$^0$ is excluded, and X denotes sulfur or in which R$^0$ denotes a straight-chain or branched alkyl group having 1-20 C atoms and X denotes oxygen, and A$^-$ has a meaning indicated for the formula (1) or a meaning indicated as preferred or particularly preferred.

Preference is given in accordance with the invention to a group of salts of the formula (1) in which R$^0$ denotes a straight-chain or branched alkyl group having 1-20 C atoms, which may be partially or fully fluorinated, X=S, and the substituents R each, independently of one another, denote a straight-chain or branched alkyl group having 1-20 C atoms, and A$^-$ has a meaning indicated for the formula (1) or a meaning indicated as preferred or particularly preferred.

Preference is given in accordance with the invention to a group of salts of the formula (1) in which R$^0$ denotes a straight-chain or branched alkyl group having 1-20 C atoms, X=O, and the substituents R each, independently of one another, denote a straight-chain or branched alkyl group having 1-20 C atoms, and A$^-$ has a meaning indicated for the formula (1) or a meaning indicated as preferred or particularly preferred.

The present invention secondly relates to a process for the preparation of the salts having thiouronium or uronium cations of the general formula (1) according to the invention. To this end, a thiourea C(S)(NR$_2$)$_2$ or a urea C(O)(NR$_2$)$_2$ is alkylated using an ester AR$^0$ or using an oxonium salt (R$^0$)$_3$O$^+$A$^-$.

The groups and substituents R$^0$ and R here are defined like those of the general formula (1) or have a meaning indicated especially. A, in the case of the reaction with the ester, can be selected from the group [R$^1$CH$_2$OSO$_3$], [R$^1$SO$_3$], [R$^F$SO$_3$], [R$^F$C(O)O] and [CCl$_3$C(O)O], and A$^-$, in the case of the reaction with the oxonium salt, can be selected from the group [(FSO$_2$)$_3$C]$^-$ and [BF$_4$]$^-$.

The reaction is preferably carried out at a temperature at which at least one of the components is liquid. The reaction is particularly preferably carried out in a temperature range in which the reaction mixture is liquid.

The reaction of the thiourea or urea with an ester or an oxonium salt can be carried out in polar organic solvents, for example 1,2-dichloroethane or dichloromethane, in nonpolar organic solvents, for example hexane or pentane, or without solvents, for example in the salt melt. In accordance with the invention, solvent mixtures can also be used instead of pure solvents.

In accordance with the invention, the reagents can be reacted with a mixing ratio of up to a five-fold excess of one of the reactants. However, the reactants are preferably employed in equimolar amount.

The salts according to the invention can be isolated with very good yields, generally above 80%, preferably above 90%.

The present invention furthermore relates to an alternative process for the preparation of a salt according to the invention by means of salt exchange. In this, a salt having a thiouronium or uronium cation of the general formula (1) and an anion A$^-$ selected from the group [BF$_4$]—, Br$^-$, Cl$^-$, I$^-$ or [ClO$_4$]$^-$ is reacted with a salt Kt$^+$A$^-$ or with an acid AH, where Kt is an alkali or alkaline earth metal and A is defined in accordance with the general formula (1).

The reaction is preferably carried out at a temperature at which at least one of the components is liquid. The reaction is particularly preferably carried out in a temperature range in which the reaction mixture is liquid.

The salt exchange of the thiouronium or uronium salt can be carried out in polar solvents, for example water, acetonitrile, dimethoxyethane, dimethylformamide, methanol or propionitrile, in nonpolar organic solvents, for example dichloromethane, or without solvents, for example in the salt melt. In accordance with the invention, solvent mixtures can also be used instead of pure solvents.

In accordance with the invention, the reagents can be reacted with a mixing ratio of up to 10% excess of one of the reactants. However, the reactants are preferably employed in equimolar amount.

The salts of the formula (1) according to the invention in which the anion A$^-$=[R$^F$$_2$P(O)O]$^-$ can alternatively be prepared by the reaction of a tris(perfluoroalkyl)phosphine oxide with an alcohol and a thiourea C(S)(NR$_2$)$_2$ or a urea C(O)(NR$_2$)$_2$, where the radicals R are as defined above and are more strongly basic than the alcohol.

The suitable alcohol is selected so that the desired cation is formed after the alkylation of the base used.

The tris(perfluoroalkyl)phosphine oxides used can be prepared by conventional methods known to the person skilled in the art. These compounds are preferably prepared by reaction with hexamethyldisiloxane (V. Ya Sememii et al, J. Gen. Chem. USSR (Engl. Trans.) 55, No. 12 (1985), 2415-2417).

All compounds according to the invention have a salt-like character, relatively low melting points (usually below 100° C.) and can be used as ionic liquids.

The salts according to the invention can be employed as solvents for many synthetic or catalytic reactions, for example Friedel-Crafts acylation and alkylation, Diels-Alder cycloadditions, hydrogenation and oxidation reactions, Heck reactions. Furthermore, it is possible to synthesise, for example, fluorinated solvents for secondary and primary batteries.

It is also possible to use the compounds according to the invention as non-aqueous electrolyte, if desired in combination with other electrolytes known to the person skilled in the art.

In addition, the salts according to the invention can be used as non-aqueous polar substances in suitable reactions as phase-transfer catalyst, as surfactant (surface-active agent) or as medium for the heterogenisation of homogeneous catalysts.

The complete disclosure content of all applications, patents and publications mentioned above and below is incorporated into this application by way of reference.

Even without further comments, it is assumed that a person skilled in the art will be able to utilise the above description in the broadest scope. The preferred embodiments and examples should therefore merely be regarded as descriptive disclosure which is absolutely not limiting in any way.

The NMR spectra were measured on solutions in deuterated solvents at 20° C. on a Bruker Avance DRX spectrometer with a 5 mm $^1$H/BB broadband head with deuterium lock. The measurement frequencies of the various nuclei are: $^1$H: 300.13 MHz, $^{11}$B: 96.92 MHz, $^{19}$F: 282.41 MHz and $^{31}$P: 121.49 MHz. The referencing method is indicated separately for each spectrum or each data set.

EXAMPLE 1

N,N,N',N'-tetramethyl-S-ethylisothiouronium triflate

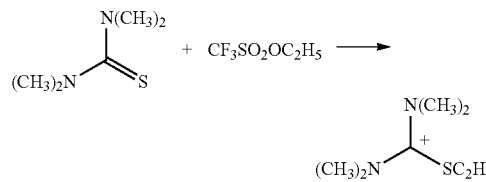

15.0 g (113.4 mmol) of N,N,N',N'-tetramethylthiourea are dissolved in 50 cm$^3$ of dichloromethane, and 20.6 g (115.6 mmol) of ethyl triflate, CF$_3$SO$_2$OC$_2$H$_5$, are added slowly (dropwise) over the course of 30 min with cooling using an ice bath while the reaction mixture is stirred vigorously using a magnetic stirrer. The reaction mixture is stirred at room temperature for a further 10 min. The solvent is removed under reduced pressure. The residue is washed three times with 30 cm$^3$ of pentane and dried for one hour at 40-50° C. under a vacuum of 7.0 Pa, giving 35.0 g of a crystalline material which melts easily. The yield of N,N,N',N'-tetramethyl-N''-ethylisothiouronium triflate is 99.5%, based on N,N,N',N'-tetramethylthiourea.

$^{19}$F NMR (reference: CCl$_3$F—internal standard; solvent: CD$_3$CN): −77.84 s (CF$_3$).

$^1$H NMR (reference: TMS; solvent: CD$_3$CN): 1.30 t (CH$_3$); 3.02 q (CH$_2$); 3.25 s (4CH$_3$); $^3J_{H,H}$=7.4 Hz.

Elemental Analysis

| | | | |
|---|---|---|---|
| Found, %: | C 30.82 | H 5.49 | N 9.07 |
| Calculated for C$_8$H$_{17}$F$_3$N$_2$O$_3$S$_2$, %: | C 30.96 | H 5.52 | N 9.03 |

EXAMPLE 2

N,N,N',N'-tetramethyl-S-ethylisothiouronium tris(pentafluoroethyl)trifluorophosphate

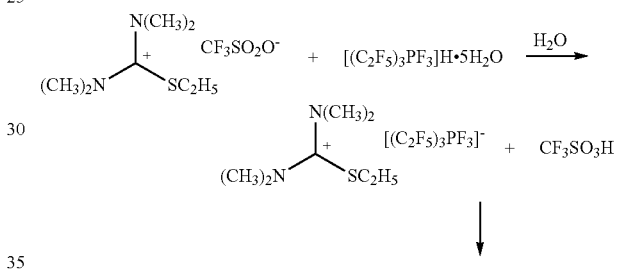

17.1 g (55.1 mmol) of N,N,N',N'-tetramethyl-S-ethylisothiouronium triflate are dissolved in 70 cm$^3$ of water, and 31.0 g (57.8 mmol) of tris(pentafluoroethyl)trifluorophosphoric acid pentahydrate are added at room temperature while the reaction mixture is stirred vigorously using a magnetic stirrer. The lower liquid phase is separated and washed four times with 30 cm$^3$ of water. The residue is dried for three hours at 60° C. in an oil bath under a vacuum of 7.0 Pa, giving 30.0 g of a liquid material. The yield of N,N,N',N'-tetramethyl-S-ethylisothiouronium tris(pentafluoroethyl)trifluorophosphate is 89.8%, based on N,N,N',N'-tetramethyl-S-ethylisothiouronium triflate.

$^{19}$F NMR (reference: CCl$_3$F—internal standard; solvent: CD$_3$CN): −43.56 dm (PF); −79.58 m (CF$_3$); −81.27 m (2CF$_3$); −86.92 dm (PF$_2$); −114.93 m (CF$_2$); −115.52 m (2CF$_2$); $^1J_{P,F}$=890 Hz; $^1J_{P,F}$=904 Hz; $^2J_{P,F}$=86 Hz; $^2J_{P,F}$=97 Hz.

$^1$H NMR (reference: TMS; solvent: CD$_3$CN): 1.34 t (CH$_3$); 3.03 q (CH$_2$); 3.25 s (4CH$_3$); $^3J_{H,H}$=7.4 Hz.

$^{31}$P NMR (reference: 85% H$_3$PO$_4$; solvent: CD$_3$CN): −148.55 dtm; $^1J_{P,F}$=890 Hz; $^1J_{P,F}$=902 Hz.

Elemental Analysis

| | | | |
|---|---|---|---|
| Found, %: | C 25.63 | H 2.87 | N 4.59 |
| Calculated for C$_{13}$H$_{17}$F$_{18}$N$_2$PS, %: | C 25.75 | H 2.83 | N 4.62 |

EXAMPLE 3

N,N,N',N'-tetramethyl-S-(2,2,2-trifluoroethyl) isothiouronium triflate

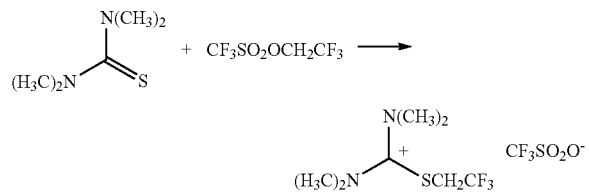

1.0 g (7.56 mmol) of N,N,N',N'-tetramethylthiourea are dissolved in 20 cm³ of hexane, and 1.84 g (7.93 mmol) of 2,2,2-trifluoroethyl triflate, $CF_3SO_2OCH_2CF_3$, are added slowly (dropwise) at room temperature while the reaction mixture is stirred vigorously using a magnetic stirrer. The reaction mixture is stirred at room temperature for a further 6 hours. The lower phase is separated from the hexane and washed twice with 10 cm³ of hexane. The residue is dried for two hours at 50° C. under a vacuum of 1.3 Pa, giving 2.74 g of an oily material (m.p. 69-70° C.). The yield of N,N,N',N'-tetramethyl-S-(2,2,2-trifluoroethyl)isothiouronium triflate is 99.4%, based on N,N,N',N'-tetramethylthiourea.

$^{19}F$ NMR (reference: $CCl_3F$—internal standard; solvent: $CD_3CN$): −65.98 t ($CF_3$); −77.92 t ($CF_3$); $^3J_{H,F}$=9.6 Hz.

$^1H$ NMR (reference: TMS; solvent: $CD_3CN$): 3.30 s (4$CH_3$); 3.75 q ($CH_2$); $^3J_{H,F}$=9.6 Hz.

EXAMPLE 4

N,N,N',N'-tetramethyl-S-ethylisothiouronium tetrafluoroborate

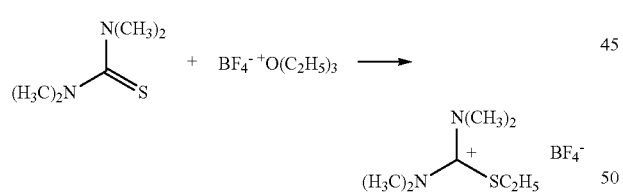

70 cm³ of a 1M solution of triethyloxonium tetrafluoroborate (69.6 mmol) in dichloromethane are added to 4.6 g (34.8 mmol) of N,N,N',N'-tetramethylthiourea while the reaction mixture is stirred vigorously using a magnetic stirrer and with ice-bath cooling. The reaction mixture is stirred at room temperature for 6 hours, and all volatile components are removed under reduced pressure. The residue is washed three times with 40 cm³ of hot (60° C.) hexane and dried for one hour at room temperature under a vacuum of 1.3 Pa, giving 6.8 g of a solid material. The yield of N,N,N',N'-tetramethyl-S-ethylisothiouronium tetrafluoroborate is 78.8%, based on N,N,N', N'-tetramethylthiourea.

$^{19}F$ NMR (reference: $CCl_3F$—internal standard; solvent: $CD_3CN$): −150.34 s; 150.40 s ($BF_4^-$).

$^1H$ NMR (reference: TMS; solvent: $CD_3CN$): 1.29 t ($CH_3$); 2.99 q ($CH_2$); 3.22 s (4$CH_3$); $^3J_{H,H}$=7.4 Hz.

EXAMPLE 5

N,N,N',N'-tetramethyl-O-methylisouronium triflate

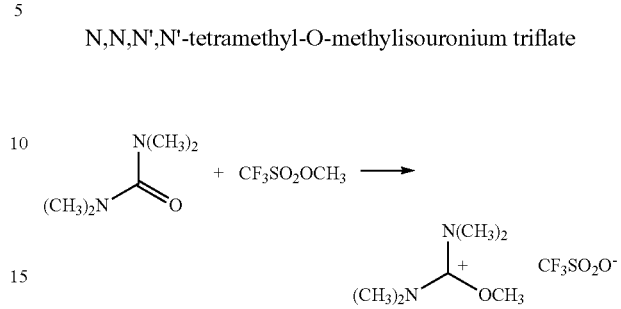

30.0 g (258.3 mmol) of N,N,N',N'-tetramethylurea are dissolved in 150 cm³ of pentane, and 43.2 g (263.3 mmol) of methyl triflate, $CF_3SO_2OCH_3$, are added slowly (dropwise) over the course of 30 minutes while the reaction mixture is cooled using an ice bath and stirred vigorously using a magnetic stirrer. The reaction mixture is stirred at room temperature for a further 10 min. The lower liquid phase is separated and washed twice with 50 cm³ of pentane. The residue is dried for one hour at 60° C. under a vacuum of 7.0 Pa, giving 71.0 g of a liquid material. The yield of N,N,N',N'-tetramethyl-O-methylisouronium triflate is 98.1%, based on N,N,N',N'-tetramethylurea.

$^{19}F$ NMR (reference: $CCl_3F$—internal standard; solvent: $CD_3CN$): −77.88 s ($CF_3$).

$^1H$ NMR (reference: TMS; solvent: $CD_3CN$): 3.05 s (4$CH_3$); 4.04 s ($CH_3$).

EXAMPLE 6

N,N,N',N'-tetramethyl-O-methylisouronium tris(pentafluoroethyl)trifluorophosphate

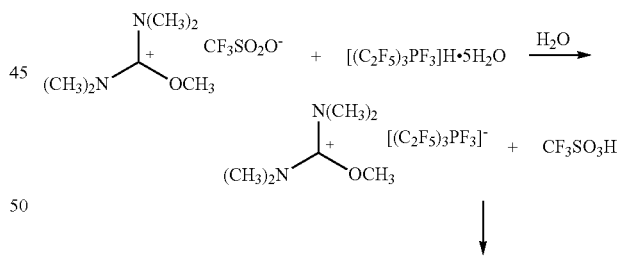

31.5 g (112.4 mmol) of N,N,N',N'-tetramethyl-O-methylisouronium triflate are dissolved in 300 cm³ of water, and 63.3 g (118.7 mmol) of tris(pentafluoroethyl)trifluorophosphoric acid pentahydrate are added at room temperature while the reaction mixture is stirred vigorously using a magnetic stirrer. The precipitate is filtered off and washed three times with 30 cm³ of water. The residue is dried for three hours at 50-60° C. in an oil bath under a vacuum of 7.0 Pa, giving 62.7 g of a solid white material (m.p. 69-70° C.). The yield of N,N,N',N'-tetramethyl-O-methylisouronium tris(pentafluoroethyl)trifluorophosphate is 96.8%, based on N,N,N',N'-tetramethyl-O-methylisouronium triflate.

$^{19}F$ NMR (reference: $CCl_3F$—internal standard; solvent: $CD_3CN$): −43.51 dm (PF); −79.54 m ($CF_3$); −81.23 m (2CF$_3$); −86.90 dm (PF$_2$); −114.90 m (CF$_2$); −115.48 m (2CF$_2$); $^1J_{P,F}$=889 Hz; $^1J_{P,F}$=901 Hz; $^2J_{P,F}$=86 Hz; $^2J_{P,F}$=98 Hz.

$^1$H NMR (reference: TMS; solvent: CD$_3$CN): 3.05 s (4CH$_3$); 4.04 s (CH$_3$).

$^{31}$P NMR (reference: 85% H$_3$PO$_4$; solvent: CD$_3$CN): −148.57 dtm; $^1J_{P,F}$=890 Hz; $^1J_{P,F}$=902 Hz.

Elemental Analysis

| Found, %: | C 24.94 | H 2.64 | N 4.89 |
| Calculated for C$_{12}$H$_{15}$F$_{18}$N$_2$OP, %: | C 25.01 | H 2.62 | N 4.86 |

EXAMPLE 7

N,N,N',N'-tetramethyl-O-ethylisouronium triflate

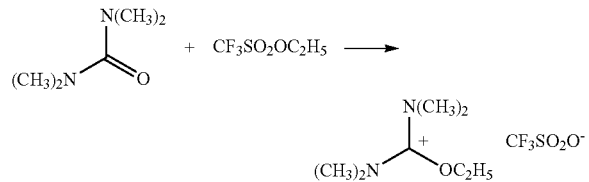

15.0 g (129.1 mmol) of N,N,N',N'-tetramethylurea are dissolved in 70 cm$^3$ of pentane, and 23.5 g (131.9 mmol) of ethyl triflate, CF$_3$SO$_2$OC$_2$H$_5$, are added slowly (dropwise) over the course of 30 minutes while the reaction mixture is cooled using an ice bath and stirred vigorously using a magnetic stirrer. The reaction mixture is stirred at room temperature for a further 10 min. The lower liquid phase is separated and washed three times with 30 cm$^3$ of pentane. The residue is dried for one hour at 50° C. under a vacuum of 7.0 Pa, giving 37.9 g of a liquid material). The yield of N,N,N',N'-tetramethyl-O-ethylisouronium triflate is 99.8%, based on N,N,N',N'-tetramethylurea.

$^{19}$F NMR (reference: CCl$_3$F—internal standard; solvent: CD$_3$CN): −77.86 s (CF$_3$).

$^1$H NMR (reference: TMS; solvent: CD$_3$CN): 1.40 t (CH$_3$); 3.05 s (4CH$_3$); 4.38 q (CH$_2$); $^3J_{H,H}$=7.1 Hz.

EXAMPLE 8

N,N,N',N'-tetramethyl-O-ethylisouronium tris(pentafluoroethyl)-trifluorophosphate

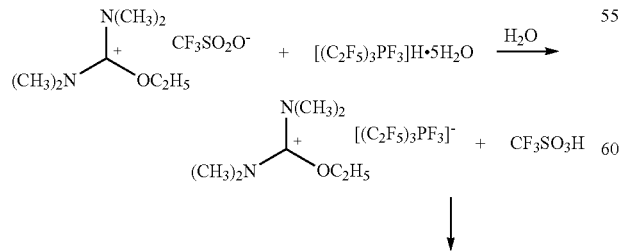

18.8 g (63.9 mmol) of N,N,N',N'-tetramethyl-O-ethylisouronium triflate are dissolved in 70 cm$^3$ of water, and 36.0 g (67.2 mmol) of tris(pentafluoroethyl)trifluorophosphoric acid pentahydrate are added at room temperature while the reaction mixture is stirred vigorously using a magnetic stirrer. The precipitate is filtered off and washed four times with 30 cm$^3$ of water. The residue is dried for three hours at 60° C. in an oil bath under a vacuum of 7.0 Pa, giving 36.7 g of a solid white material (m.p. 32-34° C.). The yield of N,N,N',N'-tetramethyl-O-ethylisouronium tris(pentafluoroethyl)trifluorophosphate is 97.3%, based on N,N,N',N'-tetramethyl-O-ethylisouronium triflate.

$^{19}$F NMR (reference; CCl$_3$F—internal standard; solvent: CD$_3$CN): −43.50 dm (PF); −79.52 m (CF$_3$); −81.21 m (2CF$_3$); −86.88 dm (PF$_2$); −114.90 m (CF$_2$); −115.48 m (2CF$_2$); $^1J_{P,F}$=889 Hz; $1J_{P,F}$=900 Hz; $^2J_{P,F}$=84 Hz; $^2J_{P,F}$=98 Hz.

$^1$H NMR (reference: TMS; solvent: CD$_3$CN): 1.42 t (CH$_3$); 3.05 s (4CH$_3$); 4.37 q (CH$_2$); $^3J_{H,H}$=7.0 Hz.

$^{31}$P NMR (reference: 85% H$_3$PO$_4$; solvent: CD$_3$CN): −148.60 dtm; $^1J_{P,F}$=888 Hz; $^1J_{P,F}$=902 Hz.

Elemental Analysis

| Found, %: | C 26.50 | H 2.95 | N 4.78 |
| Calculated for C$_{13}$H$_{17}$F$_{18}$N$_2$OP, %: | C 26.45 | H 2.90 | N 4.75 |

EXAMPLE 9

2-methyl-1,1,3,3-tetramethylisouronium bis(pentafluoroethyl)phosphinate

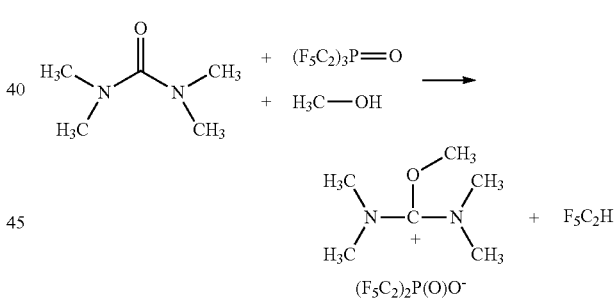

6.72 g (16.6 mmol) of tris(pentafluoroethyl)phosphine oxide, (C$_2$F$_5$)$_3$P=O, are mixed with 15 cm$^3$ of dimethoxyethane and 1.93 g (16.6 mmol) of tetramethylurea in a 25 ml flask fitted with a reflux condenser. 0.532 g (16.6 mmol) of methanol are added to this mixture while the reaction mixture is stirred using a magnetic stirrer. The reaction mixture is boiled for 5 hours, and all volatile products are removed at 50° C. under a high vacuum (1.4 Pa), giving 6.59 g of a viscous liquid. The yield of 2-methyl-1,1,3,3-tetramethylisouronium bis(pentafluoroethyl)phosphinate is 91.9%.

$^{19}$F NMR (reference; CCl$_3$F—internal standard; solvent; CD$_3$CN): −80.21 m (2CF$_3$); −124.91 dm (2CF$_2$); $^2J_{P,F}$=67 Hz.

$^1$H NMR (reference: TMS; solvent: CD$_3$CN): 3.05 s (4CH$_3$); 4.05 s (OCH$_3$).

$^{31}$P NMR (reference: 85% H$_3$PO$_4$; solvent: CD$_3$CN): −2.12 quin.; $^2J_{P,F}$=67 Hz.

The invention claimed is:

1. A uronium salt of formula (1)

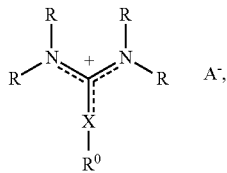

in which
X denotes O,
R and $R^0$ each, independently of one another, have the meaning of straight-chain or branched alkyl having 1-20 C atoms,
straight-chain or branched alkenyl having 2-20 C atoms and one or more double bonds,
straight-chain or branched alkynyl having 2-20 C atoms and one or more triple bonds
saturated, partially or fully unsaturated cycloalkyl having 3-7 C atoms, which are optionally substituted by one or more alkyl groups having 1-6 C atoms,
and R may also denote hydrogen,
where one or more R or $R^0$ are optionally partially or fully substituted by halogen or partially by CN or $NO_2$, but where halogenation in the α-position in $R^0$ is excluded, and
halogen denotes F, Cl, Br or I,
where R and $R^0$ may be connected to one another in pairs by a single or double bond
and where one carbon atom or two non-adjacent carbon atoms of one or more R or $R^0$ which are not directly adjacent to the hetero atom may be replaced by atoms and/or atom groups selected from the group consisting of —O—, —C(O)—, —C(O)O—, —S—, —S(O)—, —$SO_2$—, —$SO_3$—, —N=, —N=N—, —NH—, —NR'—, —PR'—, —P(O)R'—, —P(O)R'—O—, —O—P(O)R'—O—, and —P(R')$_2$=N—,
where R' is unfluorinated, partially or perfluorinated alkyl having 1-6 C atoms, saturated or partially unsaturated cycloalkyl having 3-7 C atoms, unsubstituted or substituted phenyl or an unsubstituted or substituted heterocycle,
$A^-$ is selected from the group consisting of:
$[R^1SO_3]^-$, $[R^{F'}SO_3]^-$, $[(R^FSO_2)_2N]^-$, $[(R^FSO_2)_3C]^-$, $[(FSO_2)_3C]^-$, $[R^1CH_2OSO_3]^-$, $[R^1C(O)O]^-$, $[R^{F'}C(O)O]^-$, $[CCl_3C(O)O]^-$, $[(CN)_3C]^-$, $[(CN)_2CR^1]^-$, $[(R^1O(O)C)_2CR^1]^-$, $[P(C_nF_{2n+1-m}H_m)_yF_{6-y}]^-$, $[P(C_6F_5)_yF_{6-y}]^-$, $[R^1_2P(O)O]^-$, $[R^1P(O)O_2]^{2-}$, $[(R^1O)_2P(O)O]^-$, $[(R^1O)P(O)O_2]^{2-}$, $[(R^1O)(R^1)P(O)O]^-$, $[R^F_2P(O)O]^-$, $[R^FP(O)O_2]^{2-}$, $[BF_zR^F_{4-z}]^-$, $[BF_z(CN)_{4-z}]^-$, $[B(CN)_4]^-$, $[B(C_6F_5)_4]^-$, $[B(OR^1)_4]^-$, $[N(CF_3)_2]^-$, $[N(CN)_2]^-$, $[AlCl_4]^-$ and $[SiF_6]^{2-}$,
where $R^F$ and $R^{F'}$ each, independently of one another, the meaning of
perfluorinated and straight-chain or branched alkyl having 1-20 C atoms, where the trifluoromethyl group is excluded for $R^{F'}$,
perfluorinated and straight-chain or branched alkenyl having 2-20 C atoms and one or more double bonds,
perfluorinated phenyl and saturated, partially or fully unsaturated cycloalkyl having 3-7 C atoms, which is optionally substituted by perfluoroalkyl groups,
where the $R^F$ or $R^{F'}$ are optionally connected to one another in pairs by a single or double bond and
where one carbon atom or two non-adjacent carbon atoms of $R^F$ or $R^{F'}$ which are not in the α-position to the hetero atom are optionally replaced by atoms and/or atom groups selected from the group consisting of —O—, —C(O)—, —S—, —S(O)—, —$SO_2$—, —N=, —N=N—, —NR'—, —PR'— and —P(O)R'— or optionally have an end group R'—O—$SO_2$— or R'—O—C(O)—, where R' denotes unfluorinated, partially or perfluorinated alkyl having 1-6 C atoms, saturated or partially unsaturated cycloalkyl having 3-7 C atoms, unsubstituted or substituted phenyl or an unsubstituted or substituted heterocycle
and
where $R^1$ each, independently of one another, have the meaning of hydrogen in the case where $A^-=[(CN)_2CR^1]^-$ or $[(R^1O(O)C)_2CR^1]^-$, or hydrogen in the case where $A^-=[R^1CH_2OSO_3]^-$, and R and $R^0$=alkyl groups having 1 to 20 C atoms,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which is optionally substituted by alkyl groups having 1-6 C atoms,
where $R^1$ is optionally partially substituted by CN, $NO_2$ or halogen and
halogen denotes F, Cl, Br or I,
where $R^1$ is optionally connected to one another in pairs by a single or double bond and
where one carbon atom or two non-adjacent carbon atoms of $R^1$
which are not in the α-position to the hetero atom are optionally replaced by atoms and/or atom groups selected from the group consisting of —O—, —C(O)—, —C(O)O—, —S—, —S(O)—, —$SO_2$—, —$SO_3$—, —N=, —N=N—, —NH—, —NR'—, —PR'— and —P(O)R'—, (P(O)R'O—, OP(O)R'O—, —PR'$_2$=N—, —C(O)NH—, —C(O)NR'—, —$SO_2$NH— and —$SO_2$NR'—, where R' denotes unfluorinated, partially or perfluorinated alkyl having 1-6 C atoms, saturated or partially unsaturated cycloalkyl having 3-7 C atoms, unsubstituted or substituted phenyl or an unsubstituted or substituted heterocycle and
n denotes 1 to 20,
m denotes 0, 1, 2 or 3,
y denotes 0, 1, 2, 3, or 4, and
z denotes 0, 1, 2 or 3,
with the proviso that
the anions $A^-=CF_3COO^-$ and $[B(C_6H_5)_4]^-$ are to be allowed and
$R^0$=ethyl, the anion $A^-=CH_3CH_2OSO_3^-$ is to be excluded.

2. A salt according to claim 1, wherein R is hydrogen and/or a straight-chain or branched alkyl having 1 to 12 C atoms.

3. A salt according to claim 1, wherein R is selected from the group consisting of methyl, ethyl, n-propyl, isopropyl, n-butyl, tert-butyl, sec-butyl, phenyl and cyclohexyl.

4. A salt according to claim 1, wherein $R^0$ denotes a straight-chain or branched alkyl having 1 to 12 C atoms.

5. A salt according to claim 1, wherein the anion is selected from the group consisting of $[CF_3SO_3]^-$, $[CF_3CF_2SO_3]^-$, $[CH_3CH_2SO_3]^-$, $[CF_3SO_2)_2N]^-$, $[(C_2F_5SO_2)_2N]^-$, $[(CF_3SO_2)_3C]^-$, $[(C_2F_5SO_2)_3C]^-$, $[CH_3CH_2OSO_3]^-$,

[(FSO$_2$)$_3$C]$^-$, [CF$_3$C(O)O]$^-$, [CF$_3$CF$_2$C(O)O]$^-$, [CH$_3$CH$_2$C(O)O]$^-$, [CH$_3$C(O)O]$^-$, [P(C$_2$F$_5$)$_3$F$_3$]$^-$, [P(CF$_3$)$_3$F$_3$]$^-$, [P(C$_2$F$_4$H)(CF$_3$)$_2$F$_3$]$^-$, [P(C$_2$F$_3$H$_2$)$_3$F$_3$]$^-$, [P(C$_2$F$_5$)(CF$_3$)$_2$F$_3$]$^-$, [P(C$_6$F$_5$)$_3$F$_3$]$^-$, [P(C$_3$F$_7$)$_3$F$_3$]$^-$, [P(C$_4$F$_9$)$_3$F$_3$]$^-$, [P(C$_2$F$_5$)$_2$F$_4$]$^-$, [(C$_2$F$_5$)$_2$P(O)O]$^-$, [(C$_2$F$_5$)P(O)O$_2$]$^{2-}$, [P(C$_6$F$_5$)$_2$F$_4$]$^-$, [(CF$_3$)$_2$P(O)O]$^-$, [(CH$_3$)$_2$P(O)O]$^-$, [(C$_4$F$_9$)$_2$P(O)O]$^-$, [CF$_3$P(O)O$_2$]$^{2-}$, [CH$_3$P(O)O$_2$]$^{2-}$, [(CH$_3$O)$_2$P(O)O]$^-$, [BF$_3$(CF$_3$)]$^-$, [BF$_2$(C$_2$F$_5$)$_2$]$^-$, [BF$_3$(C$_2$F$_5$)]$^-$, [BF$_2$(CF$_3$)$_2$]$^-$, [B(C$_2$F$_5$)$_4$]$^-$, [BF$_3$(CN)]$^-$, [BF$_2$CN)$_2$]$^-$, [B(CN)$_4$]$^-$, [B(CF$_3$)$_4$]$^-$, [BF$_4$]$^-$, [B(OCH$_3$)$_4$]$^-$, [B(OCH$_3$)$_2$(OC$_2$H$_5$)]$^-$, [B(O$_2$C$_2$H$_4$)$_2$]$^-$, [B(O$_2$C$_2$H$_2$)$_2$]$^-$, [B(O$_2$CH$_4$)$_2$]$^-$, [N(CF$_3$)$_2$]$^-$, [N(CN$_2$)$_2$]$^-$, [C(CN)$_3$]$^-$, [AlCl$_4$]$^-$ and [SiF$_6$]$^{2-}$.

6. A process for preparing a salt according to claim 1, comprising alkylating a urea C(O)(NR$_2$)$_2$, where R are as defined for the compound of formula (1), by an ester AR$^0$, where R$^0$ is as defined for the compound of formula (1) and A is selected from the group consisting of [R$^1$CH$_2$OSO$_3$], [R$^1$SO$_3$], [R$^F$SO$_3$], [R$^F$C(O)O] and [CCl$_3$C(O)O], where R$^1$ or R$^F$ are as defined for the compound of formula (1), or by an oxonium salt (R$^0$)$_3$O$^+$A$^-$, where R$^0$ is as defined for the compound of formula (1) and A$^-$ is selected from the group consisting of [(FSO$_2$)$_3$C]$^-$ and [BF$_4$]$^-$.

7. A process according to claim 6, wherein the alkylating reaction is carried out at a temperature at which at least one of the components is liquid.

8. A process for preparing a salt according to claim 1, comprising reacting a salt of formula (1)

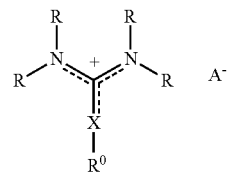

(1)

where R and R$^0$ are as defined for the compound of formula (1) and the anion A$^-$ is selected from the group consisting of [BF$_4$]—, Br—, Cl$^-$, I$^-$ and [ClO$_4$]$^-$, with a salt Kt$^+$A$^-$ or with an acid AH, where Kt is an alkali or alkaline earth metal and A is as defined for the compound of formula (1).

9. An ionic liquid composition, comprising a salt according to claim 1 and one or more compounds suitable for an ionic liquid composition.

10. A non-aqueous electrolyte composition, comprising a salt according to claim 1 and one or more compounds suitable for a non-aqueous electrolyte composition.

11. A phase-transfer catalyst composition, comprising a salt according to claim 1 and one or more compounds suitable for a phase-transfer catalyst composition.

12. A surface-active composition, comprising a salt according to claim 1 and one or more compounds suitable for a surface-active composition.

* * * * *

UNITED STATES PATENT AND TRADEMARK OFFICE
CERTIFICATE OF CORRECTION

PATENT NO. : 8,859,813 B2  Page 1 of 1
APPLICATION NO. : 13/590655
DATED : October 14, 2014
INVENTOR(S) : Ignatyev et al.

It is certified that error appears in the above-identified patent and that said Letters Patent is hereby corrected as shown below:

In the Claims

Column 17, line 53, Claim 1, reads "$F_{6-y}]^-$, $[R^1{}_2P(O)O]^-$, $[R^1P(O)O_2]O^{2-}$, $[(R^1O)_2P(O)$" should read -- $F_{6-y}]^-$, $[R^1{}_2P(O)O]^-$, $[R^1P(O)O_2]^{2-}$, $[(R^1O)_2P(O)$ --

Column 18, line 1, Claim 1, reads "where the $R^F$ or $R^{F'}$ are optionally connected to one another" should read -- where $R^F$ or $R^{F'}$ are optionally connected to one another --

Signed and Sealed this
Twenty-third Day of June, 2015

Michelle K. Lee
*Director of the United States Patent and Trademark Office*